United States Patent
Kapral

Patent Number: 5,902,573
Date of Patent: *May 11, 1999

[54] KERATIN SOFTENING TECHNIQUE AND APPARATUS

[76] Inventor: Ales M. Kapral, 12800 Reddington Rd., Tucson, Ariz. 85749

[*] Notice: This patent is subject to a terminal disclaimer.

[21] Appl. No.: 08/954,134

[22] Filed: Oct. 20, 1997

Related U.S. Application Data

[63] Continuation-in-part of application No. 08/888,948, Jul. 7, 1997.

[51] Int. Cl.$^6$ ................ A61K 7/06; A61K 7/00
[52] U.S. Cl. .................... 424/70.1; 424/401; 132/202
[58] Field of Search ............... 424/70.1, 61, 73, 424/401; 132/202

[56] References Cited

U.S. PATENT DOCUMENTS

| | | |
|---|---|---|
| 4,497,850 | 2/1985 | Umezono et al. . |
| 4,898,726 | 2/1990 | Beste .......................... 424/72 |
| 4,988,502 | 1/1991 | Ounanian et al. . |
| 5,501,733 | 3/1996 | Macaudiere et al. . |
| 5,667,768 | 9/1997 | Ramin . |
| 5,683,681 | 11/1997 | Ramin et al. . |

Primary Examiner—Sally Gardner-Lane

[57] ABSTRACT

A treatment mechanism for keratin, including hair and epidermis, in which a chemical is applied in a substantially dry state. The chemical is adapted to release sulfur from said keratin, thereby softening it. The keratin is then rinsed with water, preparing the keratin to be exfoliated from the skin or, in the case of hair, cut or shaved. The preferred chemical is a salt of fluoric acid being either tin or sodium based.

8 Claims, 3 Drawing Sheets

KERATIN SOFTENING TECHNIQUE AND APPARATUS

This is a continuation in part of U.S. patent application Ser. No. 08/888,948, entitled "An Additive for Cosmetics and Other Topically Applied Materials" filed Jul. 7, 1997.

BACKGROUND OF THE INVENTION

This invention relates generally to the cosmetic field and more particularly to additives which assist in the permeability of the cosmetic.

A wide assortment of creams, cosmetics, soaps, and medicines are applied to the topical layer of the skin with the intended affect of addressing a condition of the skin. Some examples of treatments include conditions of dry skin and acne.

The effectiveness of the treatment is directly related to the permeability of the material to the user's skin. If the active ingredient is unable to reach beneath the skin, the affect of the active ingredient is, at best, limited.

One such active ingredient is keratin which is used for the treatment of a variety of skin conditions and is also incorporated into soaps and creams to improve the user's skin. Unfortunately, keratin does not readily permeate the skin layer, hence, the vast majority of the keratin applied is simply washed or worn off without having the desired affect.

It is clear there is a need for improved cosmetic permeability.

SUMMARY OF THE INVENTION

The present invention creates a treatment mechanism for keratin, including hair and epidermis, in which a chemical is applied in a substantially dry state. While the present discussion relates generally to beards and other types of hair, the invention is intended to be used on a variety of keratin as those of ordinary skill in the art will readily appreciate from the following discussion.

Keratin is not a single substance but rather is a complex mixture of proteins. One important aspect of keratins, is the occurrence of sulfur containing diamino acid cysteine. It is this specific sulfur that distinguishes keratin from many other forms of proteins (i.e. collagen, elastin, and myofibrilla).

Cysteine is a crystalline amino acid having the formula $C_3H_7O_2NS$.

The sulfur content plays an important part in differentiating between "soft" and "hard" keratin. "Soft" keratin (i.e. corns and callouses) have less sulfur than the "hard" keratin (i.e. hair and nails).

The chemical of this invention is adapted to release sulfur from the keratin, thereby softening it. A salt of fluoric acid is the preferred sulfur releasing chemical. Sodium and tin salts of fluroic acid are particularly advantageous in this context.

The concentration of the salt of fluoric acid is kept small to avoid any side affects from its contact with the user's skin. A concentration of less than 20% is applicable, but, concentrations of less than two percent are preferred.

Once the salt of fluroic acid has contacted the keratin, the keratin is rinsed with water, thereby preparing the keratin to be exfoliated or, in the case of hair, cut or shaved.

In the case where the keratin is a callous or a thickening of the epidermis, the salt of fluroic acid softens the epidermis so that proper exfoliation of the site is easily performed.

In the case of hair or beards, the softening of the hair or beard though this invention permits the hair or beard to be cut easily and without the traditional lubricants (i.e. foam or gels).

For stiff hairs which are not to be cut, treatment using this invention renders these hairs soft and pliable.

As noted earlier, the preferred chemical is a salt of fluoric acid, and particularly a salt of either sodium or tin.

The softening of the keratin by the salt of fluroic acid is theorized to work in one of two ways:

1) The metallic salt of fluoric acid causes the protein of the keratin to loose its adherence to the sulfur. The loss of the sulfur causes the "hard" keratin to take on the attributes of a "soft" keratin; or, 2) The metallic salt of fluoric acid reacts with the sulfur (either directly with the sulfur or with the cysteine), causing the bonds between the keratin and the sulfur to be broken.

While keratins are generally not soluble, there are several instances where a keratin derivative has been rendered soluble. This has been accomplished when the disulfide linkages of the cystine were reduced and prevented from reoxidizing by alkylation of the thiol (mercaptan) groups. This was accomplished in 1934–1935 using alkylating agents having a ph greater than 12.

The present invention though goes to the other extreme by using an acid. While the solubility of the keratin is a possible explanation for reaction which has been noticed, more likely, the keratin is being rendered "soft" by the procedure of this invention.

The invention provides a keratin composition which incorporates a metallic salt of fluoric acid. The skin or nails of the user are rendered into a "soft" keratin. With the "soft" keratin, additives are more readily accepted. These additives to the skin or nails include additional keratins to thicken or replace thin skin, nails, or hair.

While the following discussion relates to keratin as an additive, those of ordinary skill in the art readily recognize that the invention is not so limited as other active ingredients are also contemplated. Keratin is the preferred active ingredient.

Products containing this invention's mixture increases the effectiveness of the additives. This increased effectiveness accomplished due to the nature of chemicals involved. While fluorides are typically stiff and brittle, they are softened significantly by the fluoric acid which also makes the keratin "softer".

In many applications, the mixture of keratin with fluoric acid needs to be suspended so that the mixture does not precipitate. Suspension is accomplished by blending the mixture with a carboxyl or a gelatin. Those of ordinary skill in the art readily recognize a variety of other additives which can be used to properly suspend the mixture.

Once the mixture has been formed using a suspension mechanism (i.e. carboxyl), it more easily spread and is readily applied to specific areas of the user's body without the keratin/fluoric acid spreading or running. One such application contemplated by this invention is the use of a suspended or gelatized mixture being applied to a user's nails to help harden and strengthen the finger or toe nails due to the added keratin.

Another application contemplated is the use of gelatized mixture for the treatment of hair and also as an additive for cosmetics.

In some embodiments of the invention, the suspended or gelatized mixture of keratin/fluoric acid is applied to a paper sheet or other suitable substrate and packaged for single use application. In this manner, the user needs only open the package and spread the keratin/fluoric acid onto the affected area to obtain the desired treatment.

Keratin is any of various albuminoids characteristic of epidermal derivatives, such as nails and feathers, which are insoluble in protein solvents, have a high sulfur content, and generally contain cystine and arginine as the predominating amino acids.

Keratin has been shown to exhibit a wide variety of desirable pharmaceutical properties such as that described in U.S. Pat. No. 4,959,213, issued to Brod et al. on Sep. 25, 1990, and entitled "Pharmaceutical Composition for Treatment and/or prevention of diseases of the skin involving an Inflammatory Process", incorporated hereinto by reference. The Brod patent describes keratin's affect on erythema and acne.

Hydrofluoric acid is an aqueous solution of hydrogen fluoride (HF). The material is typically a colorless, fuming, poisonous liquid and is extremely corrosive. It is a weak acid compared to hydrochloric acid but will attack glass and other silica materials. It is often used to polish, frost, or etch glass and to pickle copper, brass, and alloy steels, to clean stone and brick and to acidize oil wells, and also to dissolve ores.

A salt is the reaction product when a metal displaces the hydrogen of an acid. As example, sodium fluoride (NaF) is formed by adding sodium carbonate to hydrofluoric acid.

The metallic salt of hydrofluoric acid, when combined with keratin, significantly increases the passage of the keratin through the skin so that the keratin has significantly more affect.

The action of the salt of hydrofluoric acid is increased through the use of either water or alcohol. The water or alcohol provides a solvent to assist in the through mixing of the salt of hydrofluoric acid with the keratin.

The composition so formed is useful for pharmaceutical treatments, topical cleansers, soaps, creams, and as additives to a variety of cosmetics.

In the preferred embodiment, by weight, the metallic salt of hydrofluoric acid constitutes less than twenty percent of the keratin/hydrofluoric acid salt combination. The actual relative amounts are chosen to obtain the desired results for the contemplated application. Such applications include topical cosmetics, creams, soaps, and additives for pharmaceuticals.

As those of ordinary skill in the art recognize, a soap is a type of detergent in which the water-solubilizing group is a carboxylate, COO—, and the positive ion is usually sodium or potassium.

In the case of some creams, the cream, containing both keratin and the salt of hydrofluoric acid, is applied to the user's epidermal and then left to have it curative affect.

The invention, using a salt of hydrofluoric acid within a topically applied medium, significantly increases the permeability of the user's skin so that the active ingredient is more effective.

In one embodiment of the invention, the chemical is applied from a substantially dry sheet, the user then rinses the area, and is prepared to shave. The "dry" sheet is preferably packaged in a single use package which, in one embodiment of the invention, is combined in a package with a razor. This combination of chemical sheet and razor provides the user with all of the ingredients to shave and is ideal for use by hotels and airlines.

The invention, together with various embodiments thereof, will be more fully explained by the accompanying drawings and the following description.

DRAWINGS IN BRIEF

Figure 5:
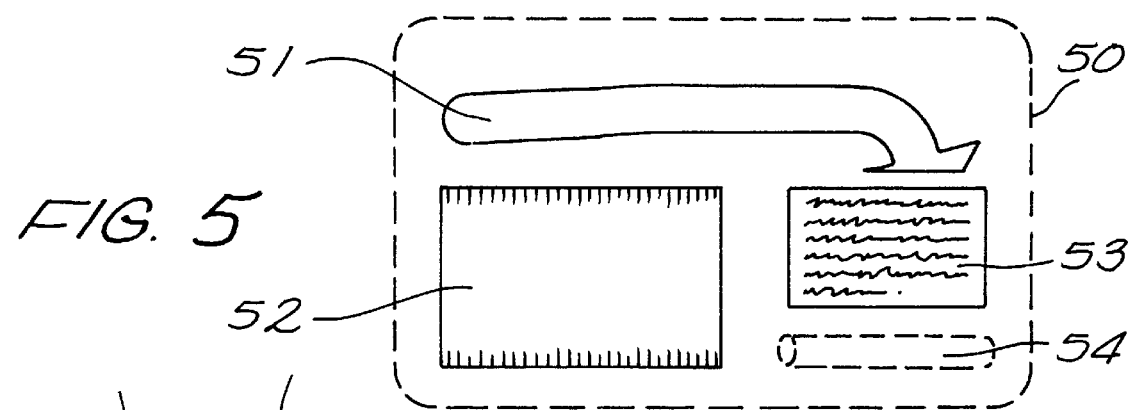

FIG. 5 diagrams the preferred kit embodiment of the invention.

Figure 6A:
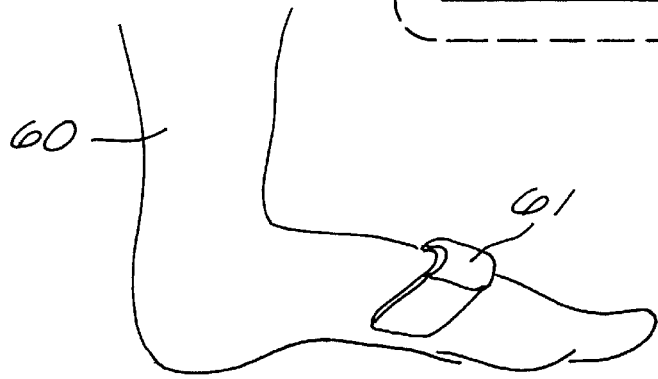
Figure 6B:
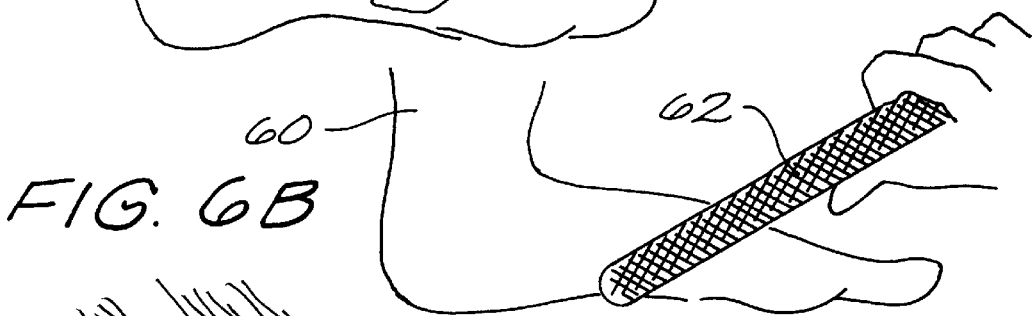

FIGS. 6A and 6B illustrate the use of the invention used to soften skin for exfoliation.

Figure 7:
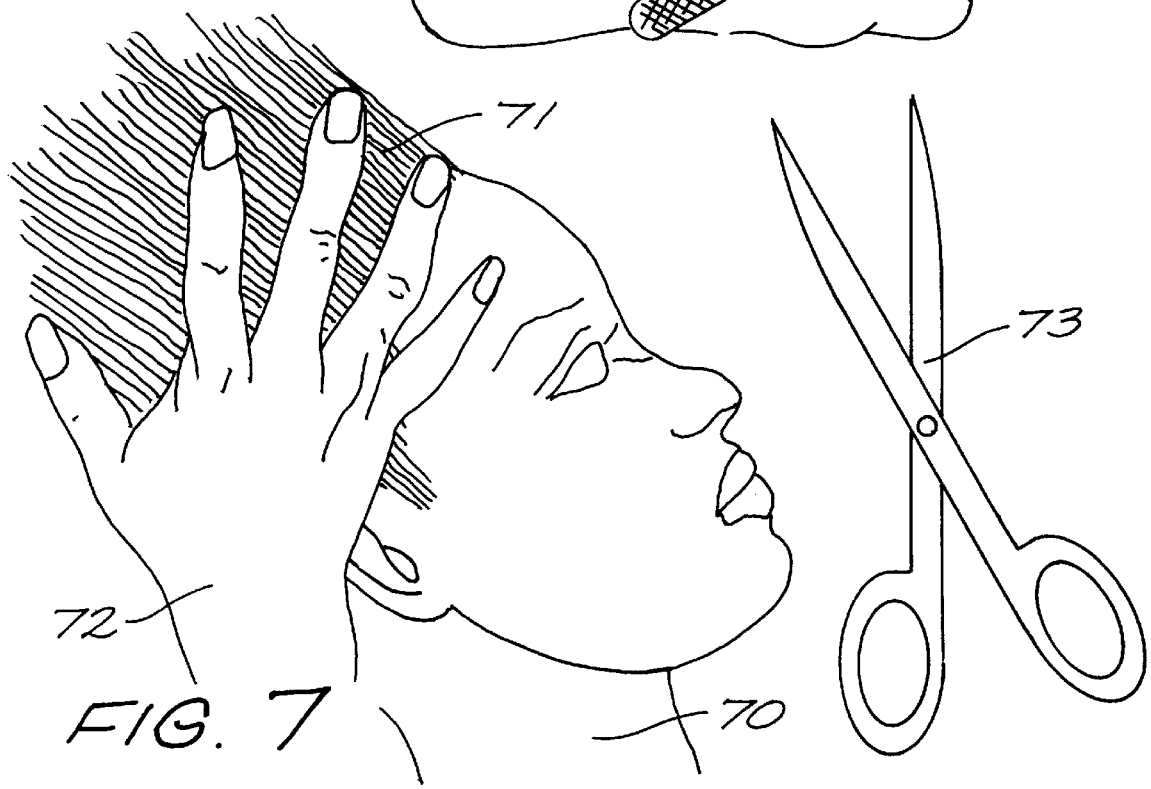

FIG. 7 illustrates the use of the invention to soften hair in preparation for cutting.

DRAWINGS IN DETAIL

Figure 1A:
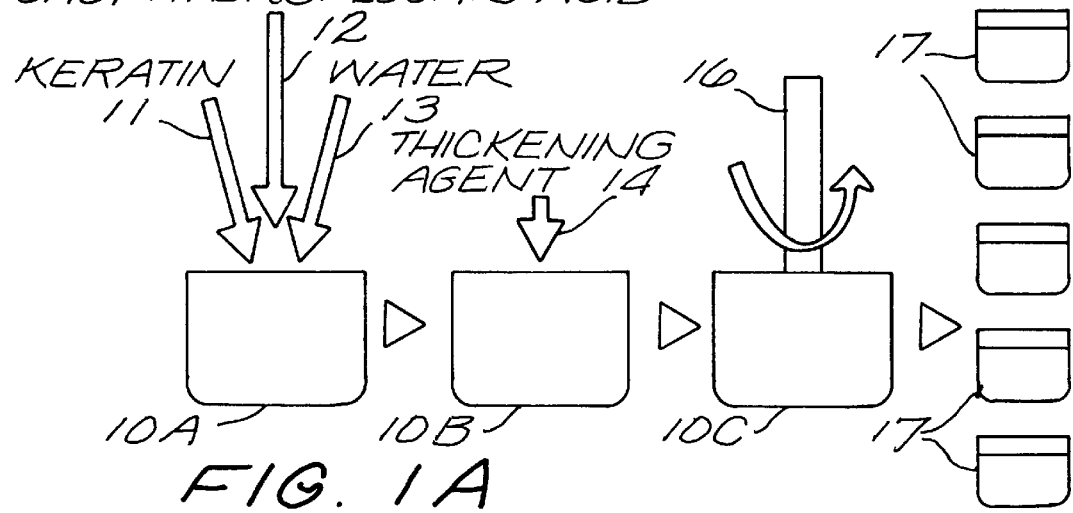
FIGS. 1A and 1B illustrate the steps taken in the production of the mixture for two embodiments of the invention.
Figure 1B:
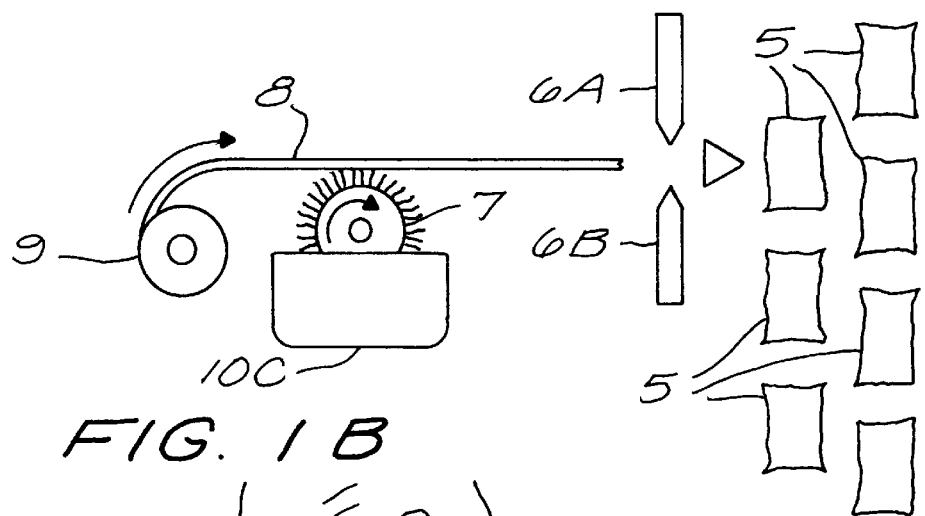

FIGS. 1A and 1B illustrate the steps taken in the production of the mixture for two embodiments of the invention.

Referring to FIG. 1A, into container 10A is placed the keratin 11, the salt of hydrofluoric acid 12, and a quantity of water 13. This mixture is the suspended through the use of a thickening agent 14 (i.e. carboxyl or a gelatin) Container 10B is then mixed 16 to form a uniform blending of the mixture.

The combination so formed, in container 10C, is then packaged 17 in small bottles for distribution to consumers.

The mixture is distributed in a different manner for the production process shown in FIG. 1B. The mixture from container 10C is applied to substrate 8 using roller 7 as substrate 8 is pulled from source roller 9.

The substrate/mixture combination is then cut by blades 6A and 6B and packaged in single use packages 5.

Figure 2:
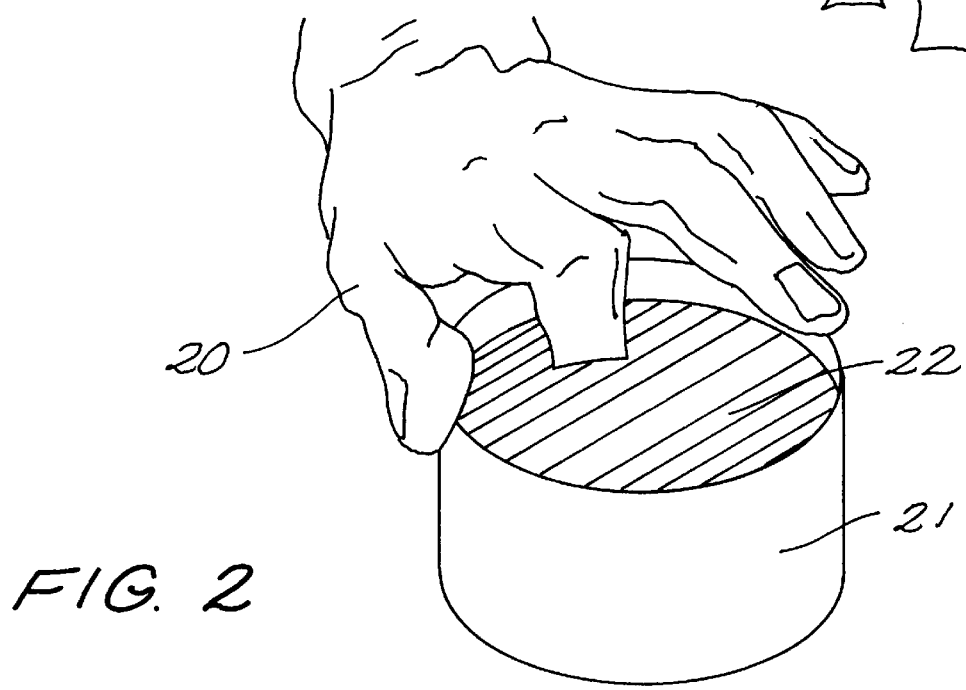
FIG. 2 illustrates an embodiment of the invention used for the treatment of nails as used in a soak arrangement.

FIG. 2 illustrates an embodiment of the invention used for the treatment of nails as used in a soak arrangement.

As illustrated, user 20 places a finger in dispenser 21 which contains a mixture 22 of keratin and salt of fluoric acid. The soaking arrangement, due to the enhanced solubility of the keratin caused by the salt of fluoric acid, readily penetrates the finger nails of user 20 so that the nails are properly treated by the keratin.

Figure 3:
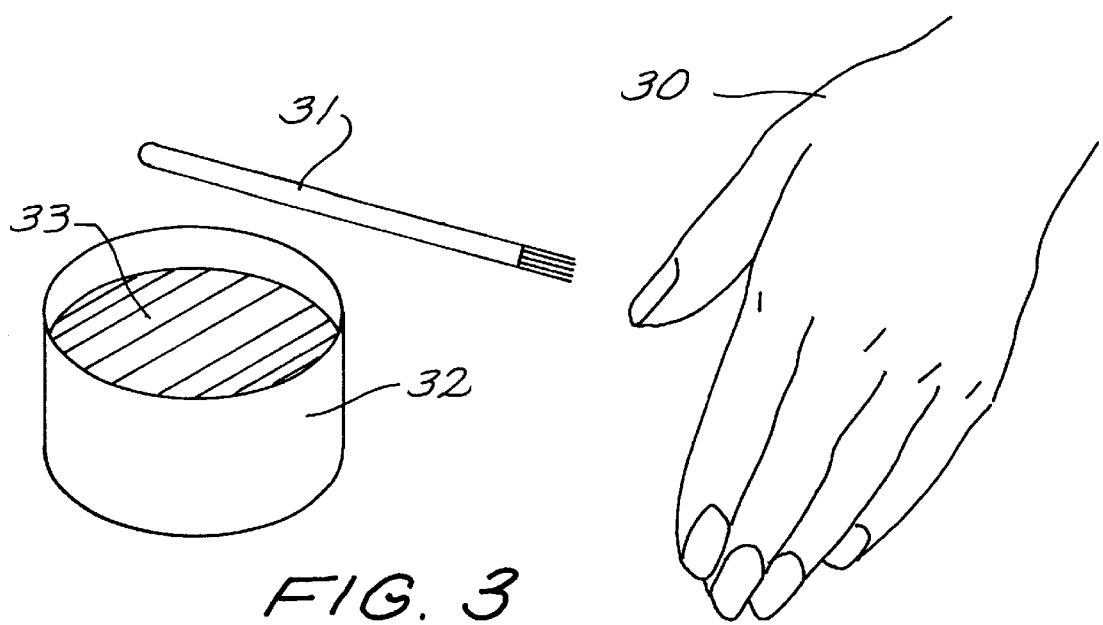
FIG. 3 illustrates an embodiment of the invention which is applied to the nails using a brush.

FIG. 3 illustrates an embodiment of the invention which is applied to the nails using a brush.

As discussed relative to FIG. 2, the combination of keratin and salt of fluoric acid is highly permeable and is beneficial for the treatment of nails and hair. In FIG. 3, application of the keratin/fluoric acid combination 33, is accomplished by using brush 31 to apply the mixture from container 32 onto the nails of user 30.

In another embodiment of the invention, the keratin/ fluoric acid mixture is combined with a soap allowing the mixture to be applied directly onto the user's hair for the strengthening of the hair.

Figure 4:
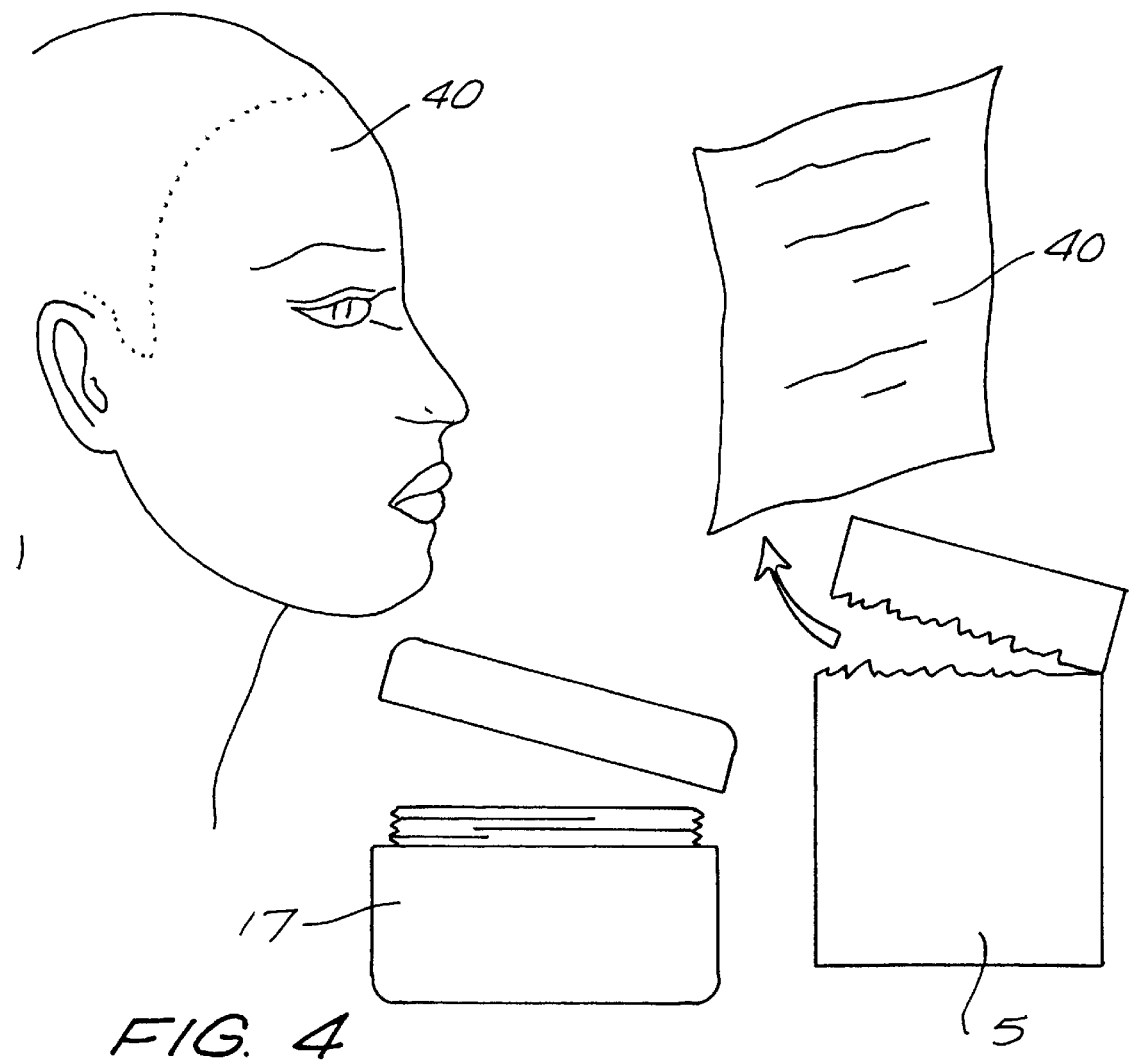
FIG. 4 illustrates two embodiments of the invention being used as a cosmetic.

FIG. 4 illustrates two embodiments of the invention being used as a cosmetic.

In this illustration, user 40 is able to apply the cosmetic from bottle 17 directly onto her face. This external topical application of the mixture of keratin/salt of fluoric acid has great therapeutic affects as the keratin has been rendered highly soluble due to the salt of fluoric acid.

As an alternative, user 40 is able to open package 5 and withdraw a single use sheet 40 which has the mixture of keratin/salt of fluoric acid thereon.

FIG. 5 diagrams the preferred kit embodiment of the invention.

This kit is particularly well suited for use by hotels and airlines and is adapted to provide a patron with all that is required for shaving. To this end, kit 50 contains a sealed envelope 52 which has contained therein, a "dry" sheet. On the "dry" sheet is impregnated the chemical (preferably salt of fluoric acid) used to release the sulfur from the beard or hair.

Kit 50 is given to the patron who uses printed instructions 53 (which may alternatively be printed onto sealed envelope 52) to receive the directions of:

(1) wipe the beard stubble with the dry sheet from the envelope;

(2) rinse the beard stubble with water; and, (3) shave with the razor.

In one embodiment of the invention, the kit also includes vial 54 which contains an aftershave liquid. Vial 54, in some embodiments of the invention is replaced by a sealed packet containing the aftershave.

This kit is also useful for trips and for guests.

FIGS. 6A and 6B illustrate the use of the invention used to soften skin for exfoliation.

As an initial step, FIG. 6A, user 60 places a bandage-like apparatus 61 over a growth or callous which is to be removed. A portion of the bandage-like apparatus has a coating of the chemical so that the area to be treated has sustained exposure to the chemical to obtain maximal softening.

The bandage-like apparatus 61 is removed and, in some embodiments, rinsed with water. Then a file 62 or other such apparatus is used to exfoliate the site. Since the site is "softened", the exfoliation process is easily accomplished.

FIG. 7 illustrates the use of the invention to soften hair in preparation for cutting.

The hair 71 of patron 70 is treated by beautician 72 by applying chemical to the hair 72. While a variety of techniques are available to apply the chemical, the preferred embodiment uses disposable gloves which have had their exterior portion treated with the chemical (such as salt of fluroic acid).

Once hair 71 has been treated, it is preferably rinsed with water and then cut by beautician 72 using scissors 73.

It is clear that the present invention creates a highly improved soluble and permeable mixture for the use in a wide variety of applications from cosmetics to nail treatment.

What is claimed is:

1. A technique for treating keratin on a user comprising the steps of:

a) applying a metallic salt of fluoric acid to said keratin; and, b) rinsing said keratin with water.

2. The technique according to claim 1, further including the step of maintaining contact between said salt of fluoric acid and said keratin for an extended period.

3. The technique according to claim 2, further including the step of exfoliating a top layer of skin from said user.

4. The technique according to claim 1, wherein said keratin is a hair and further including the step of cutting said hair after the step of rinsing said hair with water.

5. The technique according to claim 1, wherein said keratin includes hair and wherein the step of contacting said keratin with a chemical includes the step of wiping a substantially dry sheet impregnated with said salt of fluoric acid, over said keratin.

6. The technique according to claim 5, further including the step of cutting said hair.

7. The technique according to claim 6, wherein the step of cutting said hair includes the step of shaving said hair.

8. The technique according to claim 6, wherein the step of cutting said hair includes the step of trimming said hair with scissors.

* * * * *